United States Patent [19]

Courage

[11] Patent Number: 5,054,502

[45] Date of Patent: Oct. 8, 1991

[54] DEVICE AND A METHOD FOR MEASURING THE ELASTIC AND ELASTICOVISCOUS DEFORMABILITY OF SKIN

[75] Inventor: Wilfried Courage, Cologne, Fed. Rep. of Germany

[73] Assignee: Courage+Khazaka electronic GmbH, Fed. Rep. of Germany

[21] Appl. No.: 411,133

[22] Filed: Sep. 22, 1989

[30] Foreign Application Priority Data

Sep. 28, 1988 [DE] Fed. Rep. of Germany ....... 3832690

[51] Int. Cl.$^5$ .............................................. A61B 5/00
[52] U.S. Cl. .................................... 128/774; 128/633; 128/664
[58] Field of Search .................... 128/633, 660.02, 664, 128/665, 774

[56] References Cited

U.S. PATENT DOCUMENTS

| 4,580,574 | 4/1986 | Gavish | 128/774 |
| 4,850,365 | 7/1989 | Rosenthal | 128/633 |
| 4,947,851 | 8/1990 | Sarvazyan et al. | 128/774 |

FOREIGN PATENT DOCUMENTS

| 0255809 | 2/1988 | European Pat. Off. | 128/774 |
| 0337842 | 10/1989 | European Pat. Off. | 128/774 |
| 3445587 | 6/1986 | Fed. Rep. of Germany | 128/774 |
| 8401665 | 12/1985 | Netherlands | 128/665 |

Primary Examiner—Lee S. Cohen
Assistant Examiner—Krista M. Pfaffle
Attorney, Agent, or Firm—Diller, Ramik & Wight

[57] ABSTRACT

A device for measuring the elastic and elasticoviscous deformability of skin a measuring probe (1) is provided that exerts pressure on the skin surface (2) in a measuring probe channel (3), a light barrier (4) being disposed in the region of the measuring probe channel (3), the measured length 7 of which light barrier extending transversally to the measuring probe channel (3) in the region of the outlet (5) thereof. The change in light intensity serves as a measure for the deformation of the skin surface.

30 Claims, 2 Drawing Sheets

DEVICE AND A METHOD FOR MEASURING THE ELASTIC AND ELASTICOVISCOUS DEFORMABILITY OF SKIN

BACKGROUND OF THE INVENTION

The invention relates to a device and a method for measuring the elastic and elasticoviscous deformability of skin, comprising a measuring probe having a path-measuring device for measuring the deformation path of the skin surface and an electronic evaluating device, as well as to a method for measuring the elastic and plastic deformability of the human skin by pressurizing skin via a measuring probe and by measuring the deformation of the skin in response to the pressure load by measuring the deformation path.

In dermatology and cosmetics it is often necessary to perform measurements of the elasticity of skin in order to be able to check the success of therapies or the success of cosmetic preparations.

From German Patent 29 09 092 a device for measuring the elasticity of the human skin is known which includes a sensor adapted to be pressed o the skin surface with a predetermined pressure. In this device, pressure is exerted on the sensor by a presettable weight and the path of resilient intrusion of the sensor into the skin surface to be checked is determined by means of a path-measuring device. Alternatively, it is possible to provide the tip of the sensor with a suction bell that is depressurized, so that not only a pressure resistance test but also a stress test may be performed by means of the sensor. In this case, the sensor firmly adheres to the skin surface and is subsequently loaded by a weight via a turn roll such that it exerts a pulling force on the skin surface. In doing so, the path of displacement of the sensor is measured in dependence on the pulling force by means of an electronic evaluating device. Such a measuring device is mechanically complex, the measuring itself being difficult to perform for reasons of the low weights used, since for a measuring the skin surface to be checked has to lie absolutely still. Moreover, no satisfactory precision can be obtained with the device described, since at the low pressures used and the low bearing weights resulting therefrom, interference factors like the friction of the cord and the friction of the bearing of the cord roll, as well as movements of the skin surface, will be reflected in the measuring. Finally, it is necessary to have the skin surface to be checked lie in a horizontal position, because of the weights used.

Further, a device for measuring the elasticity of the human skin is known from European Patent 0 255 809 wherein a vacuum bell is placed on the skin surface to be examined, which bell is connected via a duct to a vacuum gauge device and a measuring chamber in which a piston is movably arranged. In order to depressurize the suction bell, the piston of the measuring chamber is moved backward from a defined zero position to a predetermined vacuum and the necessary suction volume, which depends on the volume of skin bulging into the suction bell, is determined at the measuring chamber. This device has the disadvantage of requiring a comparatively large skin surface for measuring the volume, thus making it impossible to measure smaller skin surfaces or different skin layers, e.g. the uppermost skin layer that is of particular importance for cosmetics.

From German Laid Open 36 12 312 a device for examining the elasticity of the skin surface is known in which the deformation of the skin is caused by subjecting the skin surface to a gas flow. The degree of deformation is determined by the reflection of light at the deformed location. A light barrier is not provided.

From French Laid Open 26 03 183 a measuring device for measuring skin characteristics is known in which an element is pressed into the skin under the action of a spring, which element enters the skin in different depths depending on the deformation of the skin. The end of the element opposite the skin influences the path of light of a light barrier in dependence on the depth of intrusion into the skin.

Further, an optic sensor is known (German Patent 87 03 658) in which emitter and receiver are disposed within a U-shaped casing, the emitter being lodged in one leg and the receiver being lodged in the other leg of the U-shaped enclosure and the passage of the beams extending vertically between these legs.

SUMMARY OF THE INVENTION

It is the object of the invention to provide a device and a method for measuring the elastic and elasticoviscous deformability of the human skin, which allows an improved accuracy of measurement and a high reproducability of the measured values, which further allows measuring the flexibility of top skin layers and which is not susceptible to shocks.

According to the present invention, the object is solved by
the measuring probe having a channel exerting a pneumatic pressure on the skin,
disposing a light barrier in the region of the measuring probe channel for measuring the path, the measuring length of which extends transversely to the measuring probe channel to the plane of the outlet thereof.

According to the invention, it is provided with a view to the method that
the pressure is exerted pneumatically on the skin surface to be measured via a measuring probe channel,
the skin deformation is measured without contact by means of a light barrier disposed in the pressurized measuring probe channel, the change in light intensity of which is used as a measure of the deformation of the skin surface.

Disposing a light barrier in the region of the outlet of a pressurized channel allows a direct and true measurement of the skin deformation, a defined position for the initial position of the non-pressurized skin surface being given at the same time by the bearing surface of the measuring head. Such a measuring probe is not susceptible to shocks, may be inserted in any position and allows for accurate and highly reproducible measured values. Thus, deformations of the magnitude of 10 microns can be measured. Slight movements of the skin surface to be examined do not interfere with the measuring procedure.

Preferably it is provided that the measuring head of the measuring probe at least partly consists of a glass body through which the measured length extends. A measuring head of glass provides that the measured length extends immediately to the contact surface between skin and measuring head, thus allowing to measure even the slightest skin deformations.

The light emitter and the light receiver of the light barrier may be disposed on opposite sides of the measuring probe and the measured length may be deflected twice by means of mirrors. The double deflection of the measured length and the light emitters and light receivers integrated in the measuring probe allow for a compact structure of the probe and, thus, for a free mobility of the measuring probe.

In an embodiment of the invention it is provided that the measuring probe comprises an electronic circuit for controlling the light emitter and for amplifying the measuring signal of the light receiver. Processing the signal in the measuring probe directly avoids interferences in transmission or errors.

Preferably it is provided that the light emitter consists of an infrared light diode and that the light receiver is a infrared photo diode. Using infrared light avoids a disturbance of the measuring by daylight. Additionally, the infrared light may be modulated in order to exclude measuring errors caused by other infrared light.

The outlet of the channel may have a diameter of 2 to 8 mm. A small diameter of the channel outlet allows for the measuring of the flexibility of the top skin layers, whereas a larger outlet allows for the measuring of the flexibility of deeper skin layers, as well.

An embodiment of the invention provides a replaceable measuring head of the measuring probe. The replaceability of the measuring head allows the use of different channel profiles or different shapes of the outlet without requiring a separate measuring probe for each form of channel.

The measuring probe can be provided with a measuring head biased by a spring. A measuring head such biased allows for a constant and reproducible pressure of the measuring probe against the skin surface.

Preferably the measuring probe is provided as a pneumatic pressure device, including a pump, a pressure accumulator and a throttle valve, which generates the pressure in the measuring probe channel, the control of the pump, of the pressure in the pressure accumulator and the throttle valve position being performed via a microprocessor that also drives the electronic circuit of the measuring probe. The microprocessor allows for the automatic execution of single and of a plurality of directly successive measurings with different measuring pressure and measuring programs.

It is provided in a preferred embodiment that the pressure in the measuring probe channel is a vacuum. In this case, the skin surface is sucked into the measuring probe channel by the vacuum, so that direct measuring of the skin deformation without skin contact is possible.

In another embodiment it is provided that the pressure in the measuring probe channel is a pressure above atmospheric pressure and that a piston element which is freely movable in the measuring probe channel and on which the overpressure acts, contacts the skin surface with its one end and projects into the measured length of the light barrier with its other end. Thus, it is possible, by simply replacing the measuring head and by driving the pressure device correspondingly, to perform vacuum measurements or measurements of indentations of the skin surface, alternatively.

The measuring probe may be set onto the skin with the vacuum or the overpressure already present, or the pressure in the measuring probe channel may be increased from zero to a predetermined set value after the measuring probe has been applied. Moreover, it is possible to exert a changing load on the skin surface after the measuring probe has been applied, by the pressure varying several times between two limit values. It is also possible to let the pressure drop to atmospheric pressure suddenly or after a predetermined time. The device and the method according to the present invention thus allow for a variety of examination methods that can supply a maximum of information about the elastic and the elasticoviscous behavior of the skin. One important information after the pressurizing is e.g. the time-dependent residual deformation of the skin surface after the cessation of the pressure load, which is a measure for the plasticity of the skin.

BRIEF DESCRIPTION OF THE DRAWINGS

The following is a detailed description of embodiments of the invention with reference to the accompanying drawings in which.

DESCRIPTION OF THE PREFERRED EMBODIMENTS

Figure 1:
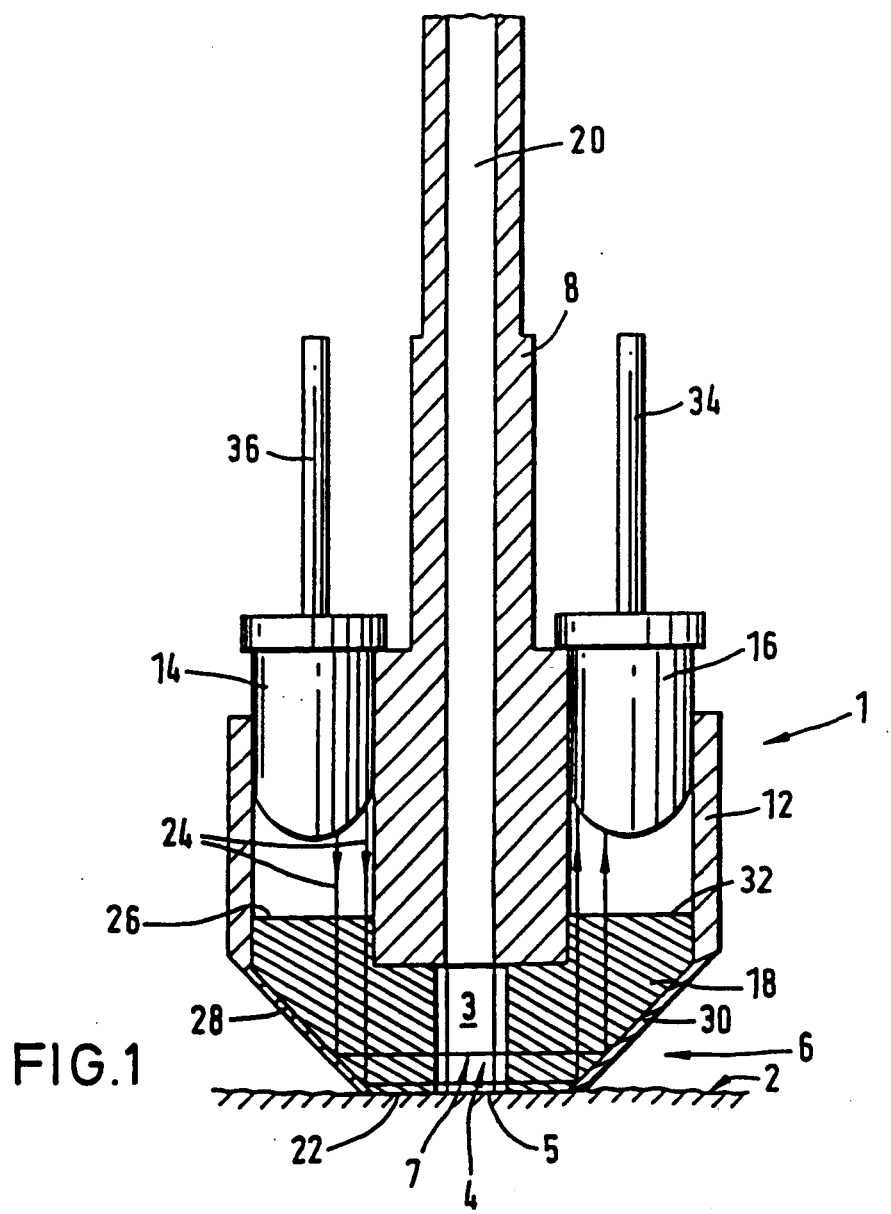
FIG. 1 is a measuring probe for causing a vacuum on the skin surface.

The measuring probe 1 (FIG. 1) substantially comprises a connection member 8 for the connection of a pneumatic pressure line 10, and of a casing 12 that encloses a measuring head 6 of the measuring probe 1. The measuring head 6 includes a light barrier 4 consisting of an infrared light diode 14 serving as a light emitter, an infrared photodiode 16 serving as a light receiver, and a glass body 18 disposed on both sides of a measuring probe channel 3. The connection member 8 has a channel 20 extending therethrough which is inserted into the glass body 18 with the channel 20 opening into the measuring probe channel 3. The measuring probe channel 3 has an outlet 5 that is flush with a bearing surface 22 of the glass member 18. The thickness of the glass body is preferably 1 mm. The glass body or glass member 18 is centrally oriented towards the measuring probe channel 3.

The infrared diodes 14, 16 serving as light emitter and light receiver extend parallel to the channel 20 or 3, respectively, the infrared light beams 24 first entering parallel to the measuring probe channel 3 through a first ground surface 26 of the glass body 18, extending rectangularly to the measuring probe channel 3. The glass body 18 has a first mirror surface 28 extending at an angle of 45° to the infrared light beams 24, which deflects the infrared light beams by 90° so that they cross the measuring probe channel 3 at an angle of 90° along a measured length 7 of the light beam. After the penetration of the measuring probe channel 3, the infrared beams 24 impinge on a second mirror surface 30 extending at an angle of 45° to the infrared light beams, which surface deflects the infrared light beams by 90° again and directs them towards the infrared, diode 16, the beams leaving the glass body at a second ground surface 32 of the glass body 18, extending transverse to the longitudinal axis of the measuring probe channel 3. The mirror surfaces 28, 30 extend to the bearing surface 22 of the glass body 18, thus allowing scanning of the measuring probe channel 3 immediately at the plane of the bearing surface 22. The mirror faces allow for the deflection of the entire light beam coming from the infrared diode 14.

The infrared diodes 14, 16 are provided with terminals 34, 36 that are connected to an electronic circuit 38 (shown in FIG. 3) to control the light emitter and to amplify the measuring signal of the light receiver, the circuit being attached to the measuring probe 1.

A vacuum acts on the channel 20 of the connection member 8, and thus on the measuring probe channel 3, via the pneumatic pressure line 10 of the embodiment shown in FIG. 1, thereby sucking the skin surface 2 into the measuring probe channel 3 at the outlet 5 to different extents, depending on the flexibility of the skin surface. This results in a weakening of the light intensity transmitted from the light emitter to the light receiver, which is used as a measuring signal for the maximum height of the skin bulge and, thereby, for the elasticity of the skin.

Figure 2:
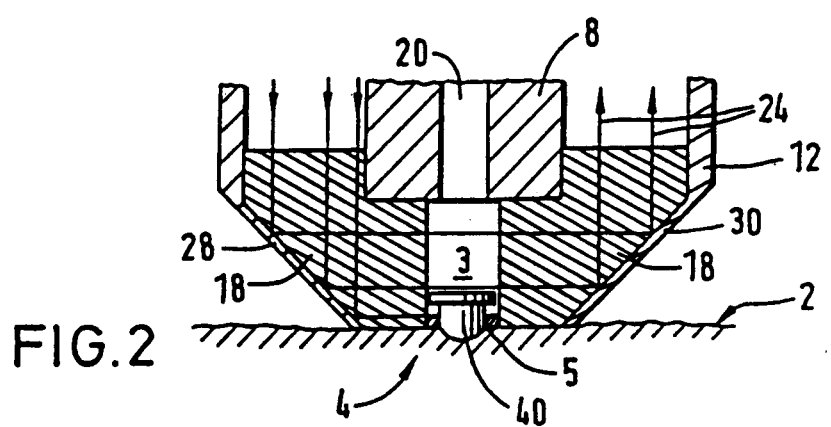
FIG. 2 is a measuring probe for causing overpressure o the skin surface and FIG. 3 is a schematic diagram of a measuring device comprising a measuring probe, a pressure generator and a microprocessor.

FIG. 2 illustrates another embodiment in which the channel 20 and the measuring channel 3 are pressurized, whereby a movable piston element 40 is pressed into the skin surface 2. The pressurized end of the movable piston element 40 protrudes into the measured length 7 of the light barrier 4 and, depending on the degree of indentation of the skin surface 2, influences the light intensity transmitted from the light emitter to the light receiver. The end of the piston element pressing on the skin surface can be of a straight cylindrical shape, calotte-shaped or pointed.

Figure 3:
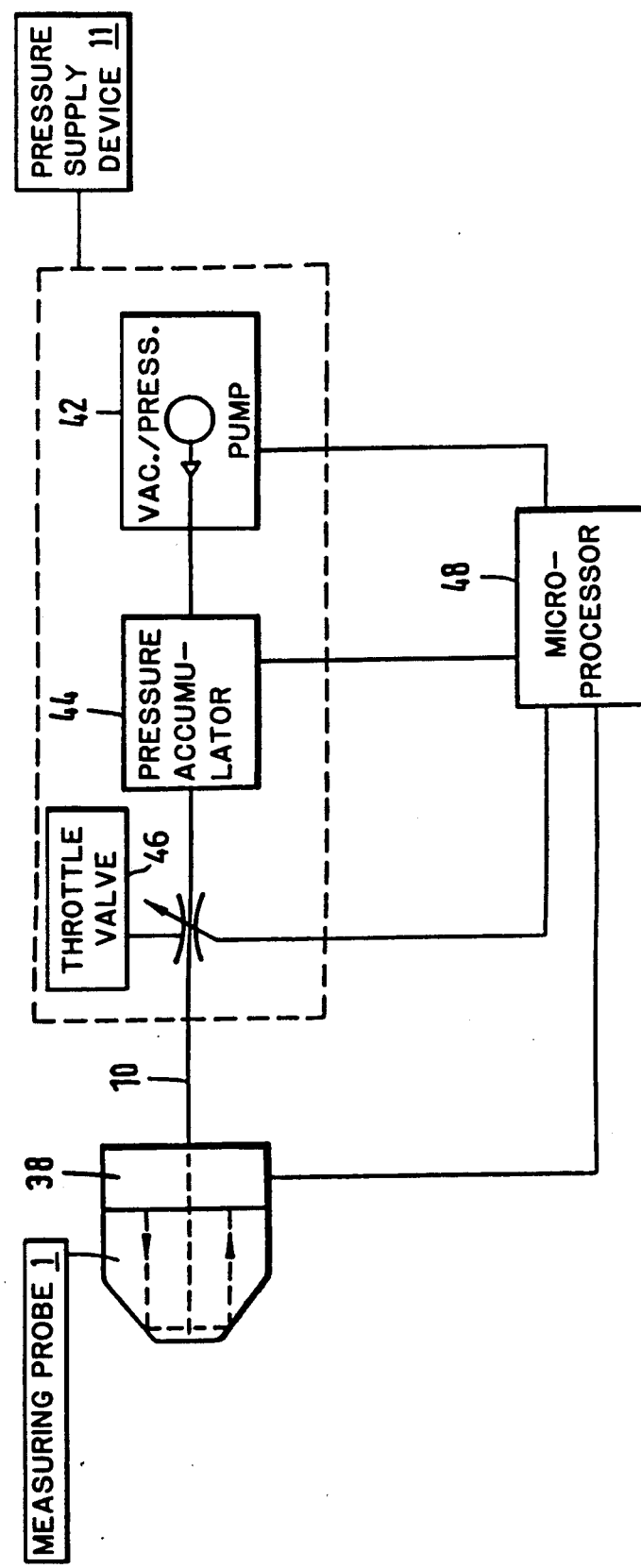

FIG. 3 illustrates a schematic diagram of the device. The measuring head 1 is connected with a pressure supply device 11 via the pneumatic pressure duct 10 which is a silicone hose, which device can alternatively supply overpressure or vacuum. The pressure supply device 11 comprises a vacuum or pressure pump 42, a pressure accumulator 44 and a drivable throttle valve 46.

The pressure accumulator 44 has a capacity of about 1 liter, whereas the pump 42 can generate a pressure of up to 500 millibars.

A microprocessor 48 controls the operation of the pump 42, monitors the pressure in the pressure accumulator 44 and controls the throttle valve 46 and drives the electronic circuit 38 at the measuring head 1 according to a predetermined program.

A particular sequence of the measurings to be performed may be set by means of the microprocessor 48, there being e.g. the following possibilities concerning the build-up of pressure:

1. Overpressure or vacuum is already present when the measuring probe is applied.
2. The vacuum is linearly increased from atmospheric pressure to a certain set value.
3. A changing pressure varying between two pressure values, e.g. nine changes in pressure load.

With reference to the decrease of pressure at the end of a measuring operation, there are the possibilities of an immediate drop in pressure and a pressure steadily falling towards the atmospheric pressure level.

The outlet 5 of the measuring probe channel 3 can have different diameters. For example, the measuring of the flexibility of the top skin layers is advantageously performed with an outlet 5 of 2 mm in diameter. For examinations of deeper skin layers, it is more advantageous to use an outlet diameter of approximately 8 mm.

In order to achieve this, it is provided that the measuring head 6 of the measuring probe 1 is adapted to be removed, so that different measuring heads with different outlets or outlet shapes can be used.

I claim:

1. A measuring probe for measuring the elastic and elasticoviscous deformability of skin comprising a measuring head (6), a measuring channel (3) in said measuring head (6), said measuring channel (3) having a first end portion adapted to be subject to pneumatic pressure and an opposite second end portion adapted to be placed in contact with the skin, means (14) for providing light to be measured, means (16) for receiving measured light, and mirror means (28, 30) for defining a light path for the provided light which is substantially normal to an axis of and in spanning relationship to said measuring channel (3) whereby skin drawn into said channel second end portion restricts the travel of the light provided along said light path.

2. The measuring probe as defined in claim 1 including a glass body (18) in said measuring head (6) which extends into said measuring channel (3).

3. The measuring probe as defined in claim 2 wherein said light providing means (14) and said measured light receiving means (16) are disposed on opposite sides of said measuring channel (3).

4. The measuring probe as defined in claim 3 including electronic circuit means (38) for controlling the light providing means (14) and for amplifying the light received by the measured light receiving means (16).

5. The measuring probe as defined in claim 2 wherein said light providing means (14) and said measured light receiving means (16) are disposed on opposite sides of said measuring channel (3), and said mirror means (28, 30) deflect the light twice during its travel between said light providing means (14) and said measured light receiving means (16).

6. The measuring probe as defined in claim 1 wherein said measuring channel sound end portion has a diameter between approximately 2 and 8 mm.

7. The measuring probe as defined in claim 1 including means for supplying pneumatic pressure to said measuring channel first end portion.

8. The measuring probe as defined in claim 1 including means for supplying pneumatic pressure to said measuring channel first end portion, said pneumatic pressure supplying means includes a pump (42), a pressure accumulator (44) and a throttle valve (46) to supply appropriate pressure to said measuring channel (3); and microprocessor means (48) for controlling said pump, pressure accumulator, throttle valve, light providing means and light receiving means.

9. The measuring probe as defined in claim 1 including means for supplying vacuum pressure to said measuring channel second end portion.

10. A measuring probe for measuring the elastic and elasticoviscous deformability of skin comprising a measuring head (6), a measuring channel (3) in said measuring head (6), said measuring channel (3) having a first end portion adapted to be subject to pneumatic pressure and an opposite second end portion adapted to be placed in contact with the skin, a piston (40) mounted for movement at said measuring channel second end portion, means (14) for providing light to be measured, means (16) for receiving measured light, and mirror mean (28, 30) for defining a light path for the provided light which is substantially normal to an axis of and in spanning relationship to said measuring channel (3) whereby said piston will be forced into said measuring channel second end portion a predetermined amount when applied against the skin thereby restricting the travel of the light provided along said light path.

11. The measuring probe as defined in claim 10 including a glass body (18) in said measuring head (6) which extends into said measuring channel (3).

12. The measuring probe as defined in claim 11 wherein said light providing means (14) and said measured light receiving means (16) are disposed on opposite sides of said measuring channel (3).

13. The measuring probe as defined in claim 12 including electronic circuit means (38) for controlling the light providing means (14) and for amplifying the light received by the measured light receiving means (16).

14. The measuring probe as defined in claim 11 wherein said light providing means (14) and said measured light receiving means (16) are disposed on opposite sides of said measuring channel (3), and said mirror means (28, 30) deflect the light twice during its travel between said light providing means (14) and said measured light receiving means (16).

15. The measuring probe as defined in claim 10 wherein said measuring channel second end portion has a diameter between approximately 2 and 8 mm.

16. The measuring probe as defined in claim 10 including means for supplying pneumatic pressure to said measuring channel first end portion.

17. The measuring probe as defined in claim 10 including means for supplying pneumatic pressure to said measuring channel first end portion, said pneumatic pressure supplying means includes a bump (42), a pressure accumulator (44) and a throttle valve (46) to supply appropriate pressure to said measuring channel (3); and microprocessor means (48) for controlling said pump, pressure accumulator, throttle valve, light providing means and light receiving means.

18. The measuring probe as defined in claim 10 including means for supplying vacuum pressure to said measuring channel second end portion.

19. A method of measuring the elastic and elasticoviscous deformability of skin comprising the steps of establishing a generally confined volume having opposite first and second end portions and a predetermined axis, generating light, directing the generated light substantially normal to the predetermined axis of the confined volume, drawing skin into the confined volume, and measuring the light traversing the confined volume as restricted by the skin to establish a measurement of the elastic and elasticoviscous deformability of the skin.

20. The method as defined in claim 19 wherein the skin drawing step is effected by creating a vacuum in the confined volume.

21. The method as defined in claim 19 wherein the skin drawing step is formed by first creating a vacuum in the confined volume and thereafter applying the confined volume against the skin.

22. The method as defined in claim 20 including the step of changing the created vacuum between first and second limits after the confined volume has been applied against the skin.

23. A method of measuring the elastic and elasticoviscous deformability of skin comprising the steps of establishing a generally confined volume having opposite first and second end portions and a predetermined axis, locating a piston in the confined volume adjacent the second end portion thereof and projecting partially there beyond, generating light, directing the generated light substantially normal tot he predetermined axis of the confined volume pushing the piston against the skin which causes the piston to recede into and restrict the confined volume, as restricted by the piston to establish a measurement of the elastic and elasticoviscous deformability of the skin.

24. The method as defined in claim 123 wherein overpressure is introduced into the confined volume which maintains the piston in its partially projecting position.

25. The method as defined in claim 24 including the step of changing the introduced overpressure between first and second limits after the piston has been pushed against the skin.

26. The method as defined in claim 23 wherein overpressure is introduced into the confined volume which maintains the piston in its partially projecting position, and the overpressure is increased from atmospheric pressure to a set value after the piston has been pushed against the skin.

27. A measuring probe for measuring the elastic and elasticoviscous deformability of skin comprising a measuring head (6), a measuring channel (3) in said measuring head (6), said measuring channel (3) having a first end portion adapted to be subject to pneumatic pressure and an opposite second end portion adapted to be placed in contact with the skin, means (14) for providing light to be measured, means (16) for receiving measured light, and mirror means (28, 30) for defining a light path for the provided light which is substantially normal to an axis of and in spanning relationship to said measuring channel (3) whereby restricted light travelling along said light path in response to placing the measuring channel second end portion against the skin constitutes a measurement of the elastic and elasticoviscous deformability of skin.

28. The method as defined in claim 27 including a glass body (18) in said measuring head (6) which extends into said measuring channel (3).

29. The method as defined in claim 27 including means for supplying pneumatic pressure to said measuring channel first end portion.

30. The method as defined in claim 27 including means for supplying vacuum pressure to said measuring channel second end portion.

* * * * *